United States Patent [19]

Lawson

[11] Patent Number: 5,366,979

[45] Date of Patent: Nov. 22, 1994

[54] ORALLY ACTIVE NONADDICTING ANALGESICS

[75] Inventor: John A. Lawson, Fremont, Calif.

[73] Assignee: Pharmaco Development Partners, Menlo Park, Calif.

[21] Appl. No.: 534,702

[22] Filed: Jun. 7, 1990

[51] Int. Cl.$^5$ ............................................. A61K 31/44
[52] U.S. Cl. ..................................... 514/282; 514/816
[58] Field of Search ................................. 514/282, 816

[56] References Cited

U.S. PATENT DOCUMENTS

| | | |
|---|---|---|
| 4,218,454 | 8/1980 | DeGraw et al. ................. 514/282 |
| 4,269,843 | 5/1981 | DeGraw et al. ................. 514/282 |
| 4,749,706 | 6/1988 | Lawson et al. ................. 514/282 |

OTHER PUBLICATIONS

Goodman & Gilman *The Pharmacological Bases of Therapeutics* 1988 p. 496.
DeGraw et al "Analgesics..." J. Medicinal Chem. vol. 21, No. 5 1978.
Burger "Medicinal Chemistry" p. 77, 1971.
Loew et al., *Chemical Abstracts*, vol. 87:127012g (1977).
Uyeno et al., *Chemical Abstracts*, vol. 88:296t (1978).
DeGraw et al., *Chemical Abstracts*, vol. 88:164212o (1978).
Uyeno et al., *Chemical Abstracts*, vol. 90:97480a (1979).
Jacobson et al., *Chemical Abstracts*, vol. 90:27684m (1983).
Manoharan et al., *Chemical Abstracts*, vol. 100:103684p (1984).
Manoharen et al., *Chemical Abstracts*, vol. 102:6882k (1985).

*Primary Examiner*—Gregory Hook
*Attorney, Agent, or Firm*—Viviana Amzel

[57] ABSTRACT

Analgesic compositions containing stereoisomerically pure normorphine and norcodeine derivatives or pharmaceutically acceptable acid addition salts thereof are described. Methods of administering the novel compositions to achieve analgesia are described as well.

24 Claims, 3 Drawing Sheets

ORALLY ACTIVE NONADDICTING ANALGESICS

TECHNICAL FIELD

This invention relates generally to the use of certain alkaloid derivatives as analgesics, and to novel pharmaceutical compositions containing those derivatives. More specifically, the invention relates to certain stereoisomerically pure N-(1'alkyl-ethyl)-normorphine and norcodeine analogs, as analgesic agents.

BACKGROUND

Large numbers of individuals in the United States and elsewhere suffer from constant debilitating pain. These individuals include victims of terminal diseases and chronic diseases such as osteoarthritis.

Ongoing attempts have been made to provide a more potent analgesic which can be self-administered and which is nonaddicting. While certain well-known and effective analgesics, such as morphine and here in, are in fact available, they lack useful oral activity and because of their potential for abuse, their use has been restricted, and the most effective forms have been denied even to terminal patients because of the vulnerability of supplies to theft.

Research to provide an effective but nonaddicting analgesic has understandably centered around structural analogs of the naturally occurring codeine and morphine compounds. A number of N-sec-alkyl analogs of normorphine have been prepared and are described in U.S. Pat. Nos. 4,269,843 and 4,218,454 to DeGraw et al., the disclosures of which are hereby incorporated by reference. A number of these N-e-methylhydrocarbyl derivatives were reported to have biological activity, and a number of them were capable of resolution into the two diastereomeric forms generated with respect to the chiral center at the α-carbon. Among those compounds which were thought at first to be incapable of resolution were N-α-methylcyclopropylmethyl normorphine (i.e., N-(1'cyclopropyl-ethyl)-normorphine) and the corresponding norcodeine compound. Resolution of these compounds was ultimately achieved as described in commonly assigned U.S. Pat. No. 4,749,706, inventors Lawson et al., also incorporated by reference herein. These compounds were found to have high analgesic activity and may be readily synthesized, i.e., using the methodology set forth in the '706 patent.

Nevertheless, there remains a need in the art for pharmaceutical compositions which have very high analgesic activity when administered either orally or parenterally, and which have a low potential for abuse. The present invention relates to such compositions, and more specifically relates to pharmaceutical compositions containing certain species of the diester intermediates described generically in U.S. Pat. No. 4,749,706 at columns 3-4, bridging paragraph, and to methods of administering those compounds and compositions so as to achieve analgesia. The present invention also relates to pharmaceutical compositions containing other, related normorphine and norcodeine analogs, and to methods of using those compounds as analgesic agents.

SUMMARY OF THE INVENTION

Accordingly, it is a primary object of the invention to address the above-mentioned need in the art, and to provide pharmaceutical compositions which are highly analgetically active when administered either orally or parenterally.

It is another object of the invention to provide such analgesic compositions which are minimally addicting.

It is still another object of the invention to provide analgesic compositions containing certain stereoisomerically pure normorphine or norcodeine derivatives that may be readily prepared in high yield, with a minimum number of synthetic steps, using normorphine or other readily available analogs as starting materials.

It is a further object of the invention to provide a method of achieving analgesia in a mammalian individual, which comprises administering the aforementioned pharmaceutical composition to the individual in an analgetically effective quantity or within the context of an analgetically effective dosage regimen.

In one aspect, the invention thus relates to pharmaceutical compositions containing stereoisomerically pure normorphine or norcodeine derivatives with high analgesic activity when orally or parenterally administered and with a low potential for abuse. These derivatives or their conventional ring (1) analogs (see below), have a 1'-alkylethyl moiety substituent at the nitrogen and are in stereochemically pure form.

In another aspect, the invention relates to method of administering a stereoisomerically pure normorphine or norcodeine derivative as will be described below so as to achieve analgesia, wherein the administration may be either oral or parenteral.

The pharmaceutical compositions of the invention contain, in combination with a pharmacologically acceptable excipient, an analgetically effective amount of a compound having the formula or a pharmaceutically acceptable acid addition salt thereof, wherein:

the dotted line indicates the presence or absence of a π bond;

R is lower alkyl;

$R^1$ is selected from the group consisting of OH, $OCH_3$, and $O(CO)R'$ where R' is $C_1$-$C_{10}$ aliphatic or aromatic hydrocarbyl or $C_4$-$C_5$ heterocyclic, and where R' may be substituted with 1-3 substituents selected so as not to interfere with analgetic activity;

$R^2$ is =O or $O(CO)R'$ where R' is as defined above; and wherein the compound of Formula I is preferably although not necessarily in a stereoisomerically pure form.

DETAILED DESCRIPTION OF THE INVENTION

Overview and Definitions:

Normorphine and norcodeine have the formula wherein, in normorphine, Y is OH, and in norcodeine, Y is $OCH_3$. It is known that certain conversions in ring (1) of codeine and morphine do not destroy biological activity. Specifically, ring (1) can be treated with a suitable reducing agent, such as hydrogen in the presence of a catalyst, to remove the ring double bond. The resulting cyclohexanol analog is active, and it can also be oxidized to obtain the cyclohexanone analog. Both the intermediate and the cyclohexanone derivative product retain activity when codeine or morphine are subjected to these reactions. In addition, conversion can be effected from the normorphine to the norcodeine analog by methylating the OH of ring (3). Methods for methylation are known in the art, for example, using phenyltrimethylammonium hydroxide (see German patent no. 247,180 (1909)), the corresponding ethoxide (Rodinor, *Bull Society Chim* (1926) 39:305) or alternative methylating agents such as methyl sulfate or methyl iodide (the choice of methylating agent will be dictated to a large extent by whether the reaction is to be carried out in an aqueous or a nonaqueous medium).

Analogs prepared using the foregoing techniques are collectively referred to herein as "conventional analogs." These conventional analogs are intended to be within the scope of the present invention.

By "stereoisomerically pure" is meant that a single one of the two diastereomers generated at the 1' carbon of the 1'-alkylethyl substituent is obtained in substantial predominance (that is greater than 90% and more preferably greater than 95% and most preferably greater than 99% of the material is the desired single diastereomer).

As further described below, upon preparation of the stereoisomerically pure forms of N-(1'-cyclopropylethyl)normorphine, it was found that one of the forms was greatly more active (about 25 times) than the other; this form has now been identified as the "R" isomer (see J. A. Lawson, "Analgesics 4. Studies on the Effects of the Introduction of Methyl at C-17 of N-Cyclopropylmethyl-Normorphine" in *Problems of Drug Dependence* 1986, Proceedings of the 48th Annual Scientific Meeting). When R is other than cyclopropyl, the difference in activity between the two stereoisomers might or might not be so marked, and the S isomer might in fact be more active than the R. Thus, the pharmaceutical compositions of the invention encompass either the R isomer of a particular compound, the S isomer, or a diastereomeric mixture thereof. By "R isomer" as used herein is intended the structure:

while the S isomer may be represented by the following structure:

The Compositions of the Invention:

The novel analgesic compositions of the invention contain one or more normorphine and/or norcodeine analogs defined by Formula I above. In Formula I:

R is lower alkyl. As used in this application, "lower alkyl" means a branched or unbranched saturated or unsaturated hydrocarbon chain containing 1-6 carbon atoms, such as methyl, ethyl, isopropyl, t-butyl, n-hexyl, and the like, as well as the cycloalkyl forms, such as cyclopropyl, methylcyclopropyl, cyclobutyl, cyclohexyl, and the unsaturated forms such as buten-2-yl, cyclohexenyl, propenyl, and so forth. Cyclopropyl is a preferred R group.

$R^1$ is selected from the group consisting of OH, $OCH_3$ and $O(CO)R'$ where R' is as defined below. Where $R^1$ is OH, the compound of Formula I is a normorphine derivative, typically a normorphine monoester. Where $R^1$ is $OCH_3$, the compound of formula 1 is a norcodeine analog, typically a norcodeine ester.

$R^2$ is =O or $O(CO)R'$. When $R^2$ is =O, the compound is a cyclohexanone derivative. When $R^2$ is =O it displaces the hydrogen atom (not shown in the structural formula) which is otherwise present at the 6-position. When $R^2$ is $O(CO)R'$, the compound of Formula I, depending on the identify of $R^1$, is either a normorphine monoester a norcodeine ester, or a normorphine diester.

R' is an organic moiety. The R' groups each contain 1-10, and preferably 1-8, carbon atoms. They can be aliphatic, aromatic, or heterocyclic. R' can be a hydrocarbyl group, that is, a group which contains only carbon and hydrogen, or it can be heteroatom-substituted, in which case it will typically be a $C_4$–$C_5$ moiety. Hydrocarbyl R' groups can include saturated alkyl-both linear and branched, cyclic alkyl, unsaturated alkyl (i.e., alkenyl), and aryl-substituted alkyls (i.e., aralkyl). Hydrocarbyl R' groups can also include aryl and alkyl-substituted aryl (i.e., alkaryl). Heteroatom-substituted R' groups can introduce heteroatoms such as oxygen or nitrogen in locations which do not interfere with the analgesic activity of the compound or with further reaction, i.e., diastereomer separation or analog conversions. A representative heteroatom R' is 2-pyridyl . Preferred R'

Preferred R' groups include saturated lower alkyl, especially methyl or ethyl; a 6-carbon aryl carrying from zero to three 1-3 carbon alkyl substituents, especially phenyl; and 2-pyridyl.

Thus, representative R' groups can include methyl (which, when taken together with the "COO" group, yields the acetic acid diester), ethyl (yielding the n-propionic acid diester), 1-ethyl-pentane (yielding the 2-ethylhexanoic acid diester), phenyl (yielding the benzoic acid diester), and the like.

The normorphine and norcodeine analogs of the invention can be conveniently classified in several groups: 1) those wherein $R^1$ and $R^2$ are O(CO)R', yielding compounds which are sometimes referred to herein, as normorphine diesters; those wherein $R^1$ is OH and $R^2$ is O(CO)R', referred to herein as the normorphine monoesters; those wherein $R^1$ is OCH$_3$ and $R^2$ is O(CO)R', giving rise to compounds referred to herein as norcodeine esters; and those wherein $R^1$ is O(CO)R' and $R^2$ is =O, i.e., the cyclohexanone analogs. For purposes of clarification, the latter compounds may be represented by the following formula:

In these cyclohexanone analogs, it is preferred that the dotted line indicate the absence of a π bond, since, as is well known, α,β-unsaturation typically gives rise to a fairly significant degree of reactivity.

Preferred compounds for use in the pharmaceutical compositions of the invention are diesters of the formula:

where R' is as defined above. Particularly preferred are diester compounds of Formula I wherein R is cyclopropyl, $R^1$ and $R^2$ are O(CO)R', and the R' are each phenyl (thus yielding the dibenzoate ester) or methyl (thus yielding the acetic acid diester).

Since the compounds of the invention are nitrogen bases, they may also be prepared as their pharmaceutically acceptable acid addition salts. "Pharmaceutically acceptable acid addition salts" refer to those salts which retain the biological effectiveness and properties of the free bases and which are not toxic or otherwise undesirable, formed with inorganic acids, such as hydrochloric acid, hydrobromic acid, phosphoric acid, and the like, or from organic acids, such as acetic acid, propionic acid, glycolic acid, oxalic acid, succinic acid, citric acid, mandelic acid, R-toluenesulfonic acid, and salicylic acid. Preferred pharmaceutically acceptable acid addition salts are the hydrochloride salts (preparation of which is exemplified in Example 4 herein).

The present pharmaceutical compositions thus contain one or more normorphine or norcodeine analogs defined hereinabove in combination with a pharmacologically acceptable excipient. Suitable excipients, vehicles and the like will be described in detail below, in the section entitled "Utility and Administration."

Preparation Methods:

The stereoisomerically pure compounds of the invention are prepared by separating the desired pure diastereomers from a mixture of the N-(1'alkyl-ethyl)normorphine (e.g., N-(1'cyclopropyl-ethyl)-normorphine) isomers by carrying out a stereoisomerically specific separation of corresponding diesters, and effecting 35 analog conversions, if desired or necessary, from the stereoisomerically pure form. The N-(1'-alkyl-ethyl)-normorphine diastereomeric mixture is first converted to a mixture of diesters by reaction with a monocarboxylic acid chloride of the formula R'COCl, where R' is as above defined. R'COCl, in turn, is obtained from the free acid using an inorganic halide such as thionyl chloride or phosphorus pentachloride, as is understood in the art. Thus, acetyl chloride is typically used to prepare the diacetate, while benzoyl chloride may be used to prepare the dibenzoate. The esterification is conducted in a suitable solvent medium containing a mild base such as, for example, pyridine, an alkylpyridine, or a trialkylamine, preferably pyridine, using as excess of the acyl halide. The resulting diesters are purified from the reaction mixture, if desired, using general standard work-up procedures.

The diastereomeric mixture of the diester is then subjected to separation into its stereoisomerically pure forms using conventional techniques known in the art, for example, chromatography on columns, or on thin layer plates, or using HPLC or differential crystallization. The precise nature of the separation method employed will depend on which diester of the normorphine derivative is chosen. For the dibenzoate, a convenient and preferred diester, differential crystallization is preferred. In this case, the more active isomer crystallizes readily from a solution containing both diastereomeric forms.

The diastereomeric mixture of the N-(1'cyclopropylethyl)-normorphines can be prepared in the manner described in U.S. Pat. Nos. 4,269,843 or 4,218,454 to DeGraw et al., cited and incorporated by reference above.

Alternatively, and preferably, stereo-isomerically pure normorphine diesters are prepared by esterification of a normorphine compound with an acid chloride R″COCl, where R″ is selected so as to give rise to a mixture of diesters that may be readily separated using, e.g., chromatography, differential crystallization, or any of the other techniques outlined above. Preferably, R″ is an aromatic substituent of 1 to 3 rings which may be either unsubstituted or substituted with 1 to 3 substituents selected so as to facilitate the isomer separation to follow. Examples of such substituents include lower alkyl, halogen, and nitro. Exemplary R″ moieties include phenyl and naphthalenyl, particularly phenyl, which gives rise to a diastereomeric mixture of dibenzoate esters. This mixture is then subjected to separation using any of the above-mentioned means, followed by ester hydrolysis, and "re-"esterification of the individual diastereomers using the desired acid chloride R'COCl wherein R' is as defined earlier. See, for example, A. Rezvani, "Synthesis in Antinociceptive Activity of 2-Cyclopropyl-Ethyl-Normorphine Compounds," submitted to the *National Narcotics Conference* and currently in press.

The aforementioned preferred reaction scheme for synthesis of the normorphine diesters of the invention is set forth in Scheme 1.

Syntheses of the other normorphine and norcodeine analogs described herein is preferably carried out according to this latter procedure, i.e., the —O(CO)R″ diester is prepared as a diastereomeric mixture, followed by separation of diastereomers, ester hydrolysis, and further conversion using the hydrolyzed single isomer as a starting material. For example, the norcodeine esters are prepared by methylation of the hydrolyzed stereoisomer using any one of a number of known methylation techniques, e.g., one of those cited earlier in this section (see Scheme 2). Preparation of the normorphine monoesters is also preferably effected through preparation of the dibenzoate intermediate, followed by separation of isomers and partial hydrolysis, preferably with a dilute base, e.g., dilute $OH^-$, carbonate, ammonia, or the like, such that the OH of the reaction is on the order of about 9 to 12. Dilute $OH^-$ is preferred. Partial hydrolysis will convert the 3-ester group to the 3-hydroxy, while the 6-ester group will be maintained (Scheme 3).

N-substitution (by which N-(1'cyclopropylethyl)-normorphine or other N-substituted derivatives of normorphine are preferably effected as described in U.S. Pat. No. 4,749,706, supra. It will be appreciated by those skilled in the art that while the synthesis set forth in Scheme 1 shows the N-substitution step carried out subsequent to the initial esterification, these steps can be performed in reverse order. In the method of the '706 patent, the desired 1'-alkyl-ethyl group is supplied as the alkyl methyl ketone of the formula $RCOCH_3$, wherein R is lower alkyl as herein defined. The ketone is added to the normorphine or conventional normorphine analog in the presence of a reducing agent, such as, for example, an alkali metal cyanoborohydride or borohydride, or via catalytic hydrogenation, preferably using sodium cyanoborohydride. The reaction is preferably carried out in the presence of an aprotic solvent and is conducted at about 50°–100° C. over the course of 10 minutes to 3 hours, preferably around 30 minutes. The reaction is quenched with weak acid to remove excess reducing agent.

Scheme 1

-continued
Scheme 1

Schemes 2 and 3

Scheme 2

Scheme 3

All of the compounds of the invention can be converted to the acid addition salts by treatment with a stoichiometric excess of the appropriate organic or inorganic acid, as set forth above. Typically, the free base is dissolved in a polar organic solvent, such as ethanol or methanol, and the acid is added, with the temperature maintained between about 0°–100° C. If the resulting acid addition salt does not precipitate spontaneously, it may be brought out of solution by addition of a less polar solvent. Of course, the acid addition salts may also be decomposed to the corresponding free base by treating with a stoichiometric excess of a suitable base, such as potassium carbonate or sodium hydroxide, typically in the presence of an aqueous solvent and at a temperature of 0°–100° C. The free base form is then isolated by conventional means, such as extraction using a less polar organic solvent.

Utility and Administration:

The compounds of Formula I are highly active analgesics which have a minimum of addicting capability. Accordingly, these compounds are useful in treating chronic pain associated with various conditions of arthritis, as well as back pain and pain associated with tumors. The compounds are also useful for ameliorating acute pain, such as that associated with surgery. The amount of the compound of Formula I administered will, of course, be dependent on the subject being treated, the severity of the pain levels, the manner of administration, and the judgment of the prescribing physician. However, an effective parenteral dose is in the range of 0.1–0.5 mg/kg/day, preferably about 0.2 mg/kg/day. For an average 70 kg human, this would amount to 7–35 mg/day, or preferably about 14 mg/day.

The administration of these active compounds and their salts can be via any of the accepted methods of administration for agents which are capable of relieving pain. These methods include, in particular, oral and parenteral or otherwise systemic forms.

As noted above, the compounds of the invention are preferably administered in a pharmaceutical composition which contains a suitable pharmacologically acceptable excipient. Also, while emphasis has been placed herein on the synthesis and identification of stereoisomerically pure compounds, it may in some cases be desirable to formulate and administer pharmaceutical compositions containing a mixture of two or more stereoisomerically pure compounds (which may or may not be a racemic mixture).

For continued administration, parenteral administration is less preferred but possible. This is characterized by injection either subcutaneously, intramuscularly, or intravenously. Injectables can be prepared in conventional forms either as liquid solutions or suspensions, solid forms suitable for solution or suspension in a liquid prior to injection, or as emulsions. Suitable excipients are, for example, water, saline, dextrose, glycerol, etc. Of course, these compositions can also contain minor amounts of nontoxic auxiliary substances, such as wetting or emulsifying agents, pH buffering agents, and so forth.

A more preferred mode of administration is oral, wherein the composition can be formulated as tablets, capsules, or syrups. Suitable pharmaceutical carriers for oral compositions include mannitol, lactose, starch, magnesium stearate, magnesium carbonate, and the like. In addition, suppositories may be formulated using, for example, polyalkylene glycols. A variety of methods for preparing dosage forms are found, for example, in Remington's Pharmaceutical Sciences, Mack Publishing Company, Easton, PA, 17th edition (1985).

It is to be understood that while the invention has been described in conjunction with the preferred specific embodiments thereof, that the foregoing description as well as the examples which follow are intended to illustrate and not limit the scope of the invention, which is defined by the scope of the appended claims.

EXAMPLE 1

Preparation of N-(1'Cyclopropyl-ethyl)-normorphine Hydrochloride

A. Preparation of N-(1'cyclopropyl-ethyl)-norcodeine: A solution of 25.3 g (0.066 mol) of N-(1-cyano)-1-ethylnorcodeine (DeGraw, J., et al., J Med Chem (1978) 21:495) in 155 mL of THF was slowly added to a solution of cyclopropyl magnesium bromide (from 49.2 g, 0.41 mol of cyclopropyl bromide and 25 g of magnesium) in 750 mL of THF. After 30 min the mixture was poured into 500 mL of 1N HCl and washed with 200 mL of Et$_2$O. The aqueous portion was made strongly alkaline with con NH$_4$OH and extracted with 250 mL of CH$_2$Cl$_2$. The extract was dried (MgSO$_4$) and evaporated to leave 16.1 g of crude product. The material was taken up in 100 mL EtOAc-EtOH (95:5) and filtered through 400 g of silica gel in a Buchner filter. The adsorbent was eluted with 3 L of the solvent followed by evaporation of the filtrate to leave 11.8 g (51%) of a yellow gum; TLC (silica gel, EtOAc-EtOH-Et$_3$N, 17:2:1) showed a single UV and I$_2$ absorbing spot at R$_f$0.50; representing the desired compound.

NMR (CDCl$_3$): 0.60(5 H, m, cyclopropyl), 1.25 (3 H, d, CH$_3$—CH), 3.80 (3 H, s, OCH$_3$), 4.90 (1 H, d, C$_5$—H), 6.50 (1 H, d, C$_1$—H), 6.70 (1 H, d, C$_2$—H).

B. N-(1'cyclopropyl-ethyl)-normorphine: To convert the norcodeine derivative prepared in Part A to the normorphine derivative, a solution of 24.7 g (0.07 mol) of N-(1'alkyl-ethyl)-norcodeine in 500 mL of dry tetrahydrofuran was treated with 25 g (0.13 mol) of diphenylphosphine and cooled to 0°–5° C. in an ice bath. Then 135 mL of 1.4 N butyl lithium in hexane was added rapidly by syringe. The mixture was allowed to warm to room temperature and then stirred at reflux for 30 min. The reaction was cooled and quenched by the slow addition of 100 mL of 2 N HCl. The solvents were evaporated in vacuo and the aqueous portion was made strongly alkaline by the addition of 2 N NaOH and again washed with 200 mL of ether. The pH was adjusted to 8–9 and the mixture extracted twice with 200 mL portions CH$_2$Cl$_2$. The extract was dried (MgSO$_4$) and evaporated in vacuo to leave 10.7 g of the crude free base. The material was chromatographed on 600 g of silica gel to afford 8.0 g (47%) of purified base.

The title hydrochloride salt was prepared in methanol by addition of aqueous hydrochloric acid and recrystallized from methanol/n-octanol, 1:7, mp 248°–250° C.

NMR (CD$_3$OD) 0.40 (1 H), m, cyclopropyl-H), 0,85 (4 H, m, cyclopropyl CH$_2$), 1.62 (3 H, d, CH$_3$CH), 4.94 (1 H, d, C$_5$—H), 5.35, 5.75 (2 H, d, C$_7$—C$_8$H's), 6.50 (1 H, d, C$_1$—H), 6.65 (1 H, d, C$_2$—H); $^{13}$C—NMR (CD$_3$O-D—DCl) 66.38, 65.32 (C$_2$'), 58.28, 58.17 (C$_9$), 23.84, 22.65 (C$_1$').

Signal heights indicated a 50:50 mixture of α,β isomers at C$_{17}$.

Anal. For C$_{21}$H$_{25}$NO$_3$•HCl•H$_2$O: Calc'd: C:64.0; H:7.12; N:3.56; Found: C:64.3; H:6.99; N:3.46.

C. In an alternative method, the normorphine derivative was directly prepared by an improved method as follows: A stirred suspension of 8.0 g (26 mM) of normorphine in 25 mL of methylcyclopropylketone and 2.5 ml of acetic acid at 90° C. was treated with excess (4.0 g; 64 mM) NaBH$_3$CN in four equal portions over 30min until the normorphine was consumed. After H$_2$ evolution ceased, the solution was cooled and glacial acetic acid added dropwise (maintaining a pH of about 5–7) until excess NaBH$_3$CN was quenched. The mixture was then partitioned between 100 mL of 3 N HCl and 20 mL of Et$_2$O. The acid extract was alkalized to pH 8–9 with con NH$_4$OH and extracted twice with 150 mL portions of Et$_2$O. The Et$_2$O was dried over MgSO$_4$ and evaporated to leave a partially crystalline residue. Trituration with Et₂O/MeOH (9:1) was followed by collection of product to afford 5.0 g (66%) of the stereoisomeric mixture.

NMR and chromatographic properties were identical to material prepared by Method B.

EXAMPLE 2

Preparation of N-(1'Cyclopropyl-ethyl)-normorphine Dibenzoate

The solution of the diastereomeric mixture prepared in part C of Example 1 (5.0 g, 14.7 mM) in 50 mL of pyridine was treated dropwise with 6.1 g (43 mM) of benzoyl chloride with maintenance of the temperature at or below 50° C. After 30 min the mixture was treated with 5 mL of CH₃OH and evaporated in vacuo. The residue was partitioned between 100 mL of CH₂Cl₂ and 50 mL of 3N HCl. The CH₂Cl₂ extract (containing the product) was washed with saturated NaHCO₃ (50 mL) and dried over MgSO₄. After filtration through a short pad of silica gel (50 g) with elution by EtOAc, the solvent was removed in vacuo to leave 6.3 g (86%) of a yellow gum. The mixture was separated by preparative HPLC on silica gel with elution by EtOAc:hexane:CH₃OH, 9:9:2). The enriched fractions were combined and evaporated to afford the A diastereomer (2.20 g, 35%) and B diastereomer (2.03 g, 32%). Each was crystallized from CH₂Cl₂/cyclohexane to give white crystals.

N-(1'cyclopropyl-ethyl)-normorphine dibenzoate (diastereomer A), mp 129–130.5, solidified, remelts 162°–164° C.; NMR (CDCl₃)δ 0.1 and 0.8 (5 H, m cyclopropyl), 1.30 (3 H, d, CH₃), 1.8–2.9 (7 H, m, C₁₀, C₁₄, C₁₅, C₁₆, C₁₉ H's), 3.10 (1 H, d, C—16H), 4.30 (1H, m, C—9H), 5.30 (1H, m, C—6H), 5.40 (1H, C—7H), 5.70 (1H, d, C—8H), 6.70 (1 H, d, C—1H), 7.00 (1 H, d, C—2H), 7.40 (6 H, m, benzoate), 8.1 (4 H, m, benzoate);

Anal. C₃₅H₃₃NO₅: Calc'd: C:76.8; H:6.03;N:2.56; Found: C:77.0; H:5.99; N:2.48.

Diastereomer B of N-(1'cyclopropyl-ethyl) normorphine dibenzoate, mp 126°–128° C. (softens) solidifies and remelts 155°–159° C.; NMR (CDCl₃): same as noted for the A-diastereomer except for the C—9H at δ 3.85 and C—6H at 3.50.

The isomers could be distinguished by TLC on silica gel, EtOAc-hexane-CH₃OH (7:7:1) with the A form (i.e., the preferred, more active isomer) at R_f 0.48 and the B form R_f 0.41.

EXAMPLE 3

Preparation of N-(1'Cyclopropyl-ethyl)-normorphine Diacetate

Figure 5:
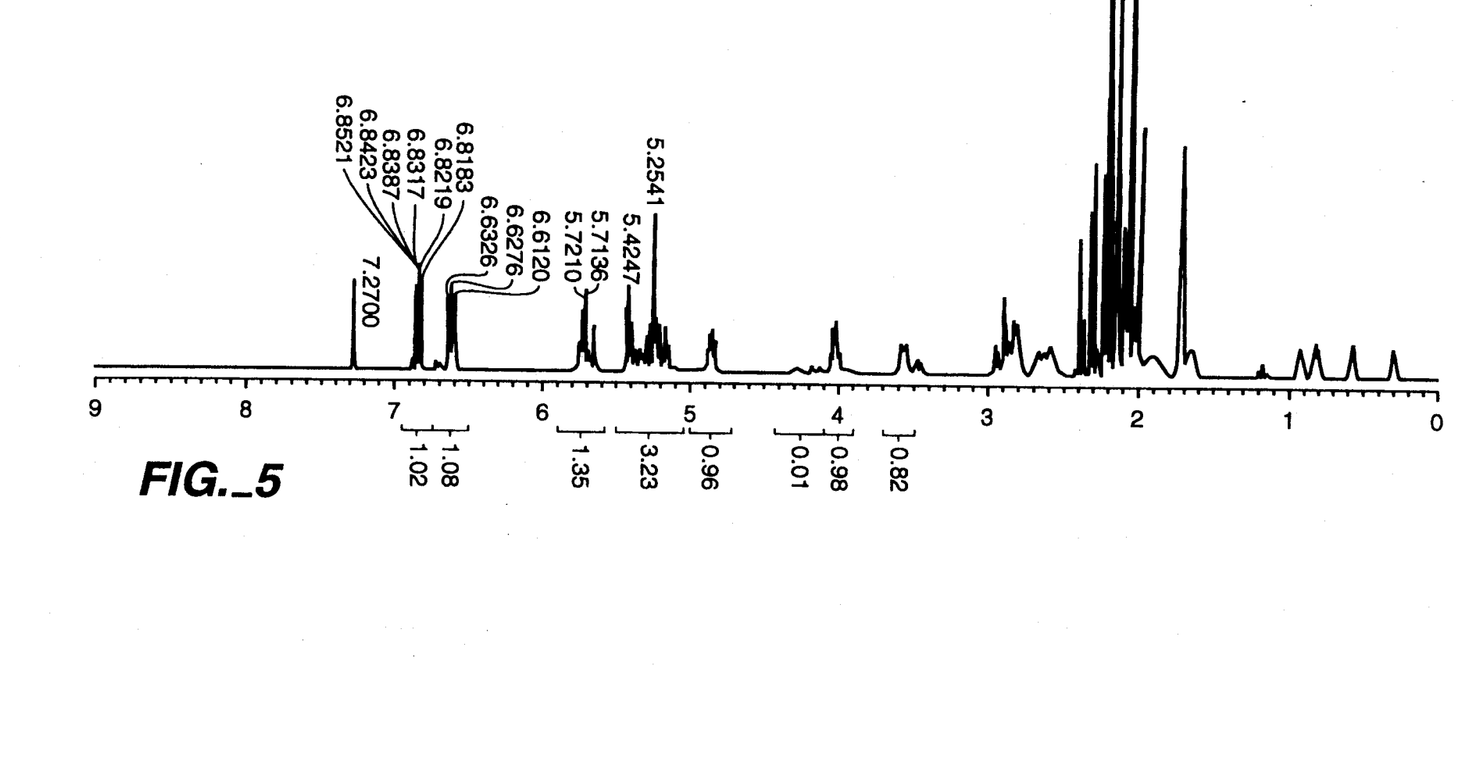
FIG. 5 is the $^1$H NMR spectrum of the product obtained in Example 3.
Figure 5A:
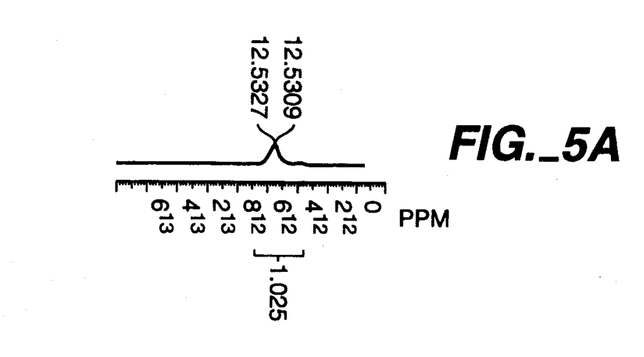

Diastereomerically pure 1LR-N-(1'cyclopropylethyl)-normorphine, isomer A as prepared in Example 1C (0.375 g, 1.0 mmole) in 5 mL CH₂Cl₂ was treated with excess triethylamine and 2.5 eq acetyl chloride. Thin layer chromatography showed the reaction to be complete after approximately 1 hr near reflux. The reaction was quenched in water, and the methylene chloride layer was separated, dried over MgSO₄, and filtered through a silica pad to give 0.417 g (98%) yellow gum. This product was dissolved in 50 mL Et₂O and precipitated with HCl/Et₂O to give a white powder, 0.393 g (85%). The product was characterized and its structure confirmed by ¹H NMR spectroscopy to be the following:

The ¹H NMR spectrum of the product is incorporated herein as FIG. 5.

EXAMPLE 4

Conversion of the diesters of Examples 2 and 3 to the corresponding HCl salts was effected by treatment with methanolic HCl (one equivalent HCl), followed by evaporation of the solvent and recrystallization with CH₂Cl₂/Et₂O.

EXAMPLE 5

Animal Studies

Groups of six ICR mice weighing 18–22 g were given either the test compounds, morphine sulfate or vehicle via a feeding needle (Harvard Apparatus MA) orally or subcutaneously. Twenty minutes later, each animal was restrained in a ventilated rigid plastic container and the nociceptive reaction in seconds was determined after tail immersion into a constant temperature water bath at 48° C. The nociceptive end-point was characterized by a jerk of the tail. The cutoff time was 15 seconds if the animal failed to respond to the hot water stimulus. The experiment was repeated every 20 min over a period of 100 to 120 min for subcutaneous and oral administration, respectively. The median antinociceptive (ED50) was determined after calculating the area under the curve for each given dose and plotted as a dose response curve. Test compounds and morphine sulfate were dissolved in distilled water, and the volume of each dose given to the animal did not exceed 0.2 ml.

Figure 1:
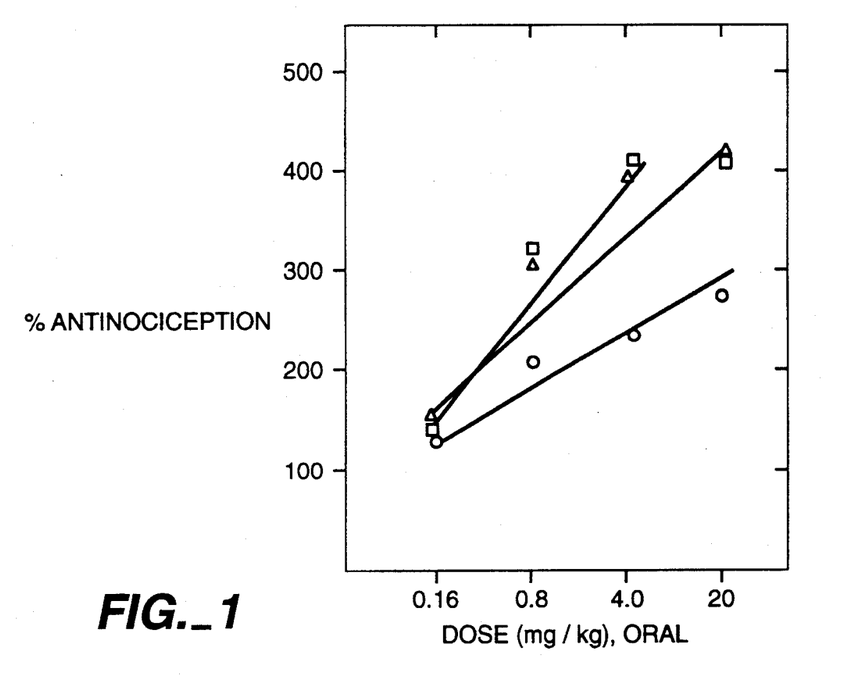
FIGS. 1 through 4 summarize graphically the results obtained in the animal studies of Example 5.
Figure 2:
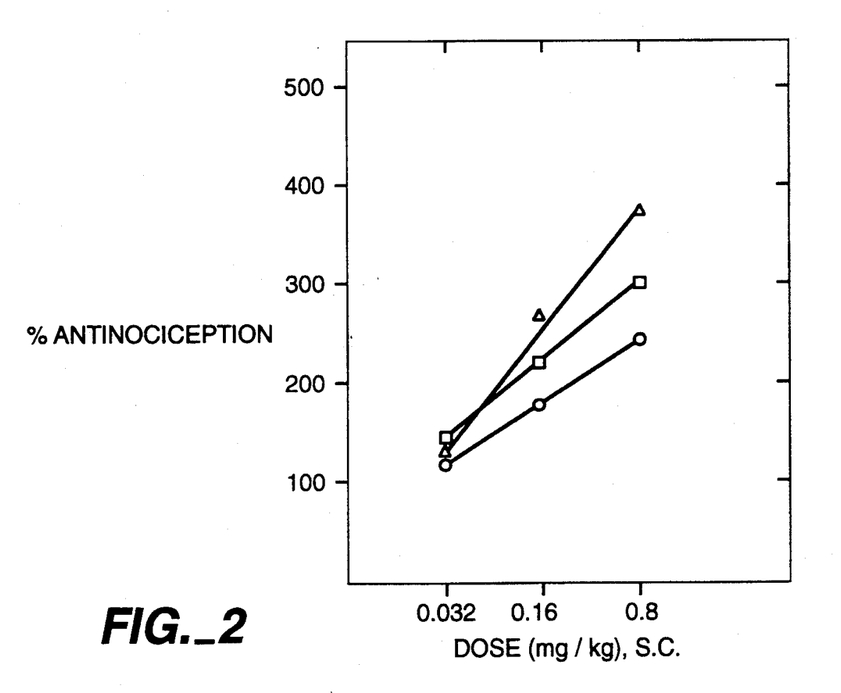
Figure 3:
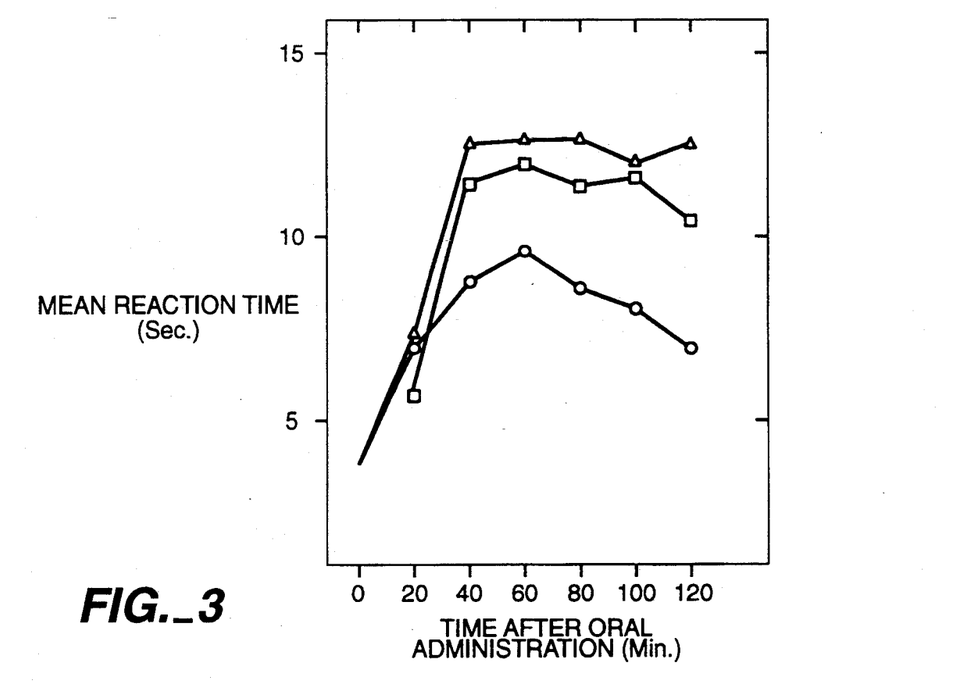
Figure 4:
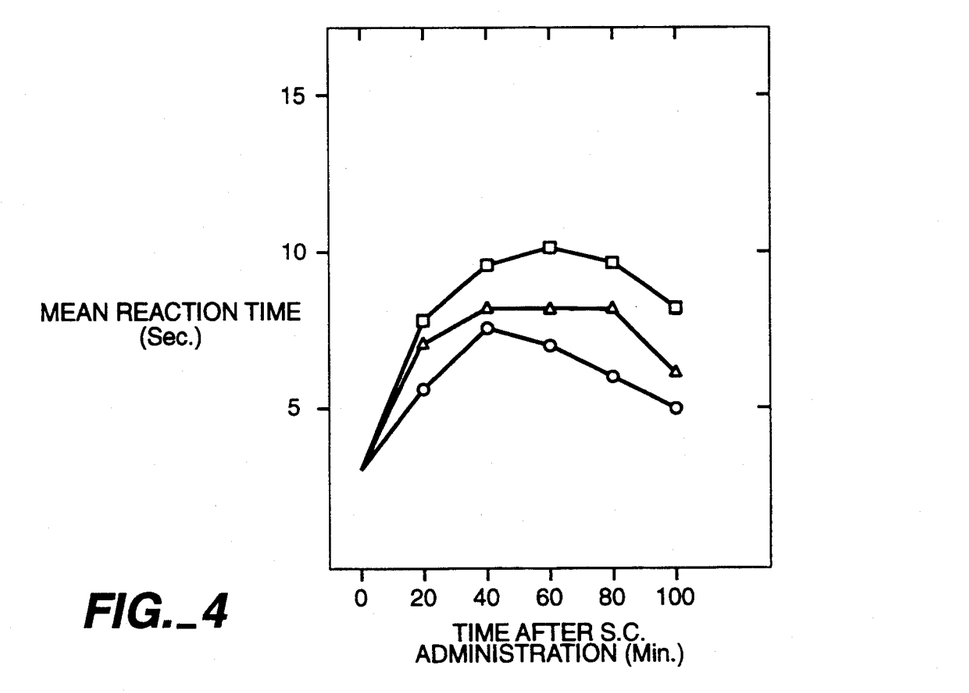

As shown in FIGS. 1 and 2, the hydrochloride salts of both the diol and diacetate forms of N-(1'cyclopropyl-ethyl)-normorphine exhibited a higher antinociceptive activity compared to morphine sulfate. The median effective dose (ED50) was found to be 0.6 mg/kg after oral and 0.16 mg/kg after subcutaneous administration. The potency ratio between the oral and subcutaneous route was calculated at 1:3.75. Single dose administration (FIGS. 3 and 4) also indicated that both compounds have a longer duration of action compared to morphine sulfate. This effect was more pronounced for the oral route; the nociception exceeded 120 min and did not return to the Pf base line.

I claim:

1. A pharmaceutical composition comprising, in combination with a pharmacologically acceptable excipient, an analgetically effective amount of a compound of the formula or a pharmaceutically acceptable acid addition salt thereof, wherein:
R is cyclopropyl or cyclobutyl; and
R' is $C_1$–$C_{10}$ aliphatic, phenyl or 2-pyridyl.

2. The composition of claim 1 wherein R' is lower alkyl.
3. The composition of claim 1 wherein R' is methyl.
4. The composition of claim 1 wherein R' is phenyl.
5. The composition of claim 1 wherein R' is 2-pyridyl.
6. The composition of claim 1 wherein R is cyclopropyl.
7. The composition of claim 1 wherein the compound of Formula I is present as a racemic mixture of stereoisomers.
8. The composition of claim 1 wherein the compound of Formula I is present in stereoisomerically pure form.
9. The composition of claim 8 wherein the stereoisomerically pure form of the compound of Formula I is the R form.
10. The composition of claim 8 wherein the stereoisomerically pure form of the compound of Formula I is the S form.
11. A method for treating pain in mammals which comprises administering to a subject in need of such treatment an effective amount of a compound of the formula or a pharmaceutically acceptable acid addition salt thereof wherein:
R is cyclopropyl or cyclobutyl; and
R' is $C_1$–$C_{10}$ aliphatic, phenyl or 2-pyridyl.

12. The method of claim 11, wherein R' is lower alkyl.
13. The method of claim 11, wherein R' is methyl.
14. The method of claim 11, wherein R' is phenyl.
15. The method of claim 11, wherein R' is pyridyl.
16. The method of claim 11, wherein R' is cyclopropyl.
17. The method of claim 11, wherein the compound is present as a racemic mixture of stereoisomers.
18. The method of claim 11, wherein the compound is present in stereoisomerically pure form.

19. The method of claim 18, wherein the stereoisomerically pure form of the compound is in the R form.
20. The method of claim 18, wherein the stereoisomerically pure form of the compound is in the S form.
21. A pharmaceutical composition, comprising, in combination with a pharmacologically acceptable excipient, an analgetically effective amount of a compound of the formula or a pharmaceutically acceptable acid addition salt thereof.

22. A pharmaceutical composition, comprising, in combination with a pharmacologically acceptable excipient, an analgetically effective amount of a compound of the formula or a pharmaceutically acceptable acid addition salt thereof.

23. A method for treating pain in mammals which comprises administering to a subject in need of such treatment an analgetically effective amount of a compound of the formula or a pharmaceutically acceptable acid addition salt thereof.

24. A method for treating pain in mammals which comprises administering to a subject in need of such treatment an analgetically effective amount of a compound of the formula or a pharmaceutically acceptable acid addition salt thereof.

* * * * *